United States Patent
Ritchey et al.

(10) Patent No.: US 10,919,038 B2
(45) Date of Patent: Feb. 16, 2021

(54) MODIFICATION OF SURFACE PROPERTIES OF MICROFLUIDIC DEVICES

(71) Applicant: Bio-Rad Laboratories, Inc., Hercules, CA (US)

(72) Inventors: Joshua Ritchey, Melrose, MA (US); Yi Xue, Shrewsbury, MA (US); Robert Meltzer, Belmont, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 141 days.

(21) Appl. No.: 15/855,913

(22) Filed: Dec. 27, 2017

(65) Prior Publication Data

US 2018/0178213 A1 Jun. 28, 2018

Related U.S. Application Data

(60) Provisional application No. 62/439,562, filed on Dec. 28, 2016.

(51) Int. Cl.
| | |
|---|---|
| *C09D 183/04* | (2006.01) |
| *B01L 3/00* | (2006.01) |
| *C09D 183/00* | (2006.01) |
| *B81C 1/00* | (2006.01) |
| *C12Q 1/686* | (2018.01) |

(52) U.S. Cl.
CPC ..... *B01L 3/50273* (2013.01); *B01L 3/502707* (2013.01); *B01L 3/502784* (2013.01); *B81C 1/00206* (2013.01); *C09D 183/00* (2013.01); *C09D 183/04* (2013.01); *B01L 2200/06* (2013.01); *B01L 2300/12* (2013.01); *B01L 2300/165* (2013.01); *B01L 2400/04* (2013.01); *C12Q 1/686* (2013.01)

(58) Field of Classification Search
CPC .................................................. C09D 183/04
See application file for complete search history.

(56) References Cited

U.S. PATENT DOCUMENTS

| | | | |
|---|---|---|---|
| 6,706,798 B2 | 3/2004 | Kobayashi et al. | |
| 10,221,321 B2* | 3/2019 | Addleman | C09D 5/00 |
| 2012/0213975 A1 | 8/2012 | Naisby et al. | |
| 2013/0291581 A1* | 11/2013 | Cox | F25C 5/06 |
| | | | 62/340 |
| 2014/0134146 A1 | 5/2014 | Olsen et al. | |
| 2015/0152270 A1 | 6/2015 | Aizenberg et al. | |
| 2015/0307759 A1* | 10/2015 | Bordoloi | C09D 7/69 |
| | | | 524/56 |

FOREIGN PATENT DOCUMENTS

| | | |
|---|---|---|
| WO | 2001/014497 A1 | 3/2001 |
| WO | 2007/133710 A2 | 11/2007 |
| WO | 2009/145022 A1 | 12/2009 |
| WO | 2017/176709 A1 | 10/2017 |

OTHER PUBLICATIONS

International Search Report and Written Opinion from PCT/US2017/068497 dated Apr. 12, 2018; 13 pages.
Hou et al.; "Hydrophobicity study of polytetrafluoroethylene nanocomposite films"; *Thin Solid Films*; vol. 520, Issue 15; Mar. 2, 2012; pp. 4916-4920.
Wu et al.; "Multilayer poly(vinyl alcohol)-adsorbed coating on poly(dimethylsiloxane) microfluidic chips for biopolymer separation"; *Electrophoresis*; vol. 26, Issue 1; Dec. 29, 2004; pp. 211-218.
Zhu et al.; "Ice-phobic Coatings Based on Silicon-Oil-Infused Polydimethylsiloxane"; *ACS Applied Materials & Interfaces*. vol. 5, Issue 10; Apr. 22, 2013; pp. 4053-4062.
Cheng, D.F. et al.; "A Statically Oleophilic but dynamically Oleophobic Smooth Nonperfluorinated Surface"; *Angew. Chem. Int. Ed*. vol. 51; 2012; pp. 2956-2959.
Cheng, D.F. et al.; "A Physical Approach to Specifically Improve the Mobility of alkane Liquid Drops"; *Journal of the American Chemical Society*. vol. 134; 2012; pp. 10191-10199.
Rabnawaz, M. et al.; "Fluorine-Free Anti-Smudge Polyurethane Coatings"; *Angew. Chem. Int. Ed*.; vol. 54; 2015; pp. 1-7.
Extended European Search Report from EP Application 17888670.1 dated Jul. 1, 2020; 9 pages.

* cited by examiner

*Primary Examiner* — William P Watkins, III
(74) *Attorney, Agent, or Firm* — Kilpatrick Townsend and Stockton LLP

(57) ABSTRACT

Compositions, devices, and methods are disclosed for the modification of polymer surfaces with coatings having a dispersion of silicone polymer and hydrophobic silica. The surface coatings provide the polymer surface with high hydrophobicity, as well as increased resistance to biofouling with proteinaceous material. The polymer surfaces can be particularly useful in microfluidic devices and methods that involve the contacting of the covalently modified polymer surfaces with emulsions of aqueous droplets containing biological macromolecules within an oil carrier phase.

10 Claims, No Drawings

MODIFICATION OF SURFACE PROPERTIES OF MICROFLUIDIC DEVICES

CROSS-REFERENCE TO RELATED APPLICATIONS

The present application claims benefit of priority to U.S. Provisional Patent Application No. 62/439,562, filed Dec. 28, 2016, the entire contents of which is incorporated herein by reference in its entirety.

BACKGROUND

Polymer surfaces typically used in the fabrication of microfluidic devices are hydrophobic in nature. This property can be very advantageous for applications in which the microfluidic device is used to handle an aqueous phase being carried in a bulk organic phase. As an example, more hydrophobic surfaces will have weaker interactions with aqueous droplets present in an oil emulsion, providing less disruption to droplet integrity and morphology. Another result of this frequently strong hydrophobicity, however, is that the polymer surfaces are more likely to capture macromolecules or other compounds present in the aqueous phase. This can cause a change in concentration, or even loss, of the compound from the aqueous phase, interfering with the proper functioning of the microfluidic device. A buildup of such captured molecules can also clog, or foul, the passage, leading to restrictions in flow and decreases in efficiency. When the captured compound is a biological macromolecule, such as a protein, the phenomenon is referred to as biofouling. Such biofouling can also negatively impact the beneficial hydrophobicity of the polymer surface, rendering it more susceptible to undesired interactions with the aqueous phase.

One approach to modifying silicon surfaces to influence their hydrophobicity or oleophobicity involves the covalent grafting of linear poly(dimethylsiloxane) (PDMS) brush films to the surfaces (Cheng et al. (2012) *J. Am. Chem. Soc.* 134:10191 and Cheng et al. (2012) *Angew. Chem. Int. Ed.* 51:2956). Because this technique relies on the covalent attachment of a polymer treatment to a surface, it is not directly applicable to many microfluidic applications. This is because microfluidic channels and devices are commonly fabricated from relatively non-reactive cyclic olefin polymer (COP) or cyclic olefin copolymer (COC) substrates.

BRIEF SUMMARY

For some microfluidic applications, it is desirable that the microfluidic surfaces be not only hydrophobic, but also non-biofouling. In this way, the surfaces within the microfluidic devices can better resist the accumulation of proteinaceous material from aqueous phase droplets. Additionally, there can be a benefit to a low-cost and easily applied surface treatment, such as a coating, that can increase the biofouling resistance of microfluidic polymer surfaces.

In general, provided herein are compositions, devices, and methods that are characterized by a surface coating that includes a silicone polymer and a hydrophobic silica dispersed within the polymer. The inventors have discovered that a mixture of silicone polymer and hydrophobic silica results in a greatly superior coating that resists biofouling compared to coatings with either ingredient alone. Treatment with this coating has been found to both enhance the desired hydrophobicity of surfaces, and to reduce undesired biofouling effects.

One provided coated polymer surface includes a substrate layer and a coating layer. The substrate layer includes a hydrophobic polymer. The coating layer includes a silicone polymer and hydrophobic silica, and is adsorbed to the substrate layer. In some embodiments, the molecular weight of the silicone polymer is within the range from 1000 Da to 10,000 Da. In some embodiments, the mass ratio of the silicone polymer to hydrophobic silica in the coating layer is within the range from 1.5:1 to 15:1. In some embodiments, the silicone polymer is polydimethylsiloxane. In some embodiments, the hydrophobic polymer is cyclic olefin polymer (COP) or cyclic olefin copolymer (COP). In some embodiments, the coated polymer surface has a water contact angle of greater than 100°. In some embodiments, the water contact angle changes by less than 10° upon exposure to an aqueous 1 mg/mL bovine serum albumin solution for 1 hour.

Also provided is a device that includes a microfluidic channel having an interior surface. The interior surface includes a coated polymer surface, wherein the coated polymer surface is in accordance with an embodiment as described herein.

Also provided is a method of moving an emulsion of droplets through a microfluidic channel, the method including providing a device that is in accordance with an embodiment as described herein. In some embodiments, the method further includes providing an emulsion including droplets and an emulsion fluid. In some embodiments, the method further includes providing a force sufficient to move the emulsion through the microfluidic channel of the device. In some embodiments, the droplets are aqueous droplets including nucleic acids and reagents sufficient for a polymerase chain reaction. In some embodiments, the emulsion fluid includes a fluorinated oil or a silicone oil.

Also provided is a method for producing a coated polymer surface, the method including contacting a substrate layer with a mixture. In some embodiments, the substrate layer includes a hydrophobic polymer. In some embodiments, the mixture includes a silicone polymer, a silicone oil, and hydrophobic silica. In some embodiments, the contacting is such that at least a portion of the silicone polymer and hydrophobic silica adsorb to the polymer surface. In some embodiments, the method further includes flushing from the substrate layer the silicone polymer, silicone oil, and hydrophobic silica not adsorbed to the substrate layer, thereby producing the coated polymer surface. In some embodiments, the coated polymer surface is an interior surface of a microfluidic channel. In some embodiments, the number average molecular weight of the silicone polymer is within the range from 1000 Da to 10,000 Da. In some embodiments, the mass ratio of silicone polymer to hydrophobic silica in the mixture is within the range from 1.5:1 to 15:1. In some embodiments, the silicone polymer is polydimethylsiloxane. In some embodiments, the molecular weight of the silicone oil is less than 500 Da. In some embodiments, the silicone oil is hexamethyldisiloxane.

In some embodiments, the method further includes washing the coated polymer surface with a fluorinated solvent. In some embodiments, the fluorinated solvent is 1,1,1,2,2,3,3,4,4-nonafluoro-4-methoxybutane. In some embodiments, the coated polymer surface has a water contact angle of greater than 100°. In some embodiments, the water contact angle changes by less than 10° upon exposure to an aqueous 1 mg/mL bovine serum albumin solution for 1 hour. In some embodiments, the hydrophobic polymer is cyclic olefin polymer (COP) or cyclic olefin copolymer (COC). In some embodiments, the flushing includes passing air over the substrate layer.

Also provided is a coating including polydimethylsiloxane and hydrophobic silica. In some embodiments, the molecular weight of the silicone polymer is within the range from 1000 Da to 10,000 Da. In some embodiments, the mass ratio of polydimethylsiloxane to hydrophobic silica in the coating layer is within the range from 1.5:1 to 15:1.

Definitions

Unless defined otherwise, technical and scientific terms used herein have the same meaning as commonly understood by a person of ordinary skill in the art. Methods, devices, and materials similar or equivalent to those described herein can be used in the practice of this invention. The following definitions are provided to facilitate understanding of certain terms used frequently and are not meant to limit the scope of the present disclosure. Abbreviations used herein have their conventional meaning within the chemical and biological arts.

"Hydrophobic" refers to a chemical compound or group having a tendency to attract non-polar or uncharged chemical groups, e.g., hexane, and to repel polar or charged chemical groups, e.g., water. "Hydrophobic" also refers to a chemical that tends not to dissolve in, mix with, or be wetted by water.

"Polymer" refers to an organic substance composed of a plurality of repeating structural units (monomeric units) covalently linked to one another.

"Coating" refers to a thin film, or layer, of material disposed on the surface of an object or substrate. Coatings will not typically have the mechanical strength to exist as stand-alone films and can be formed by applying a diluted component mixture to an object and evaporating or otherwise removing excess solvent or carrier fluid. Coatings can lie completely on the surface or can be incorporated, in whole or in part, within the openings or pores present in a substrate.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.

"Cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Heterocycloalkyl" refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Nanoparticle" refers to any solid particulate with a size that is in the range of nanometers. For example, a nanoparticle can have a diameter of less than 1 micron (1000 nm), or less than about 100 nm.

"Microparticle" refers to any solid particulate with a size that is in the range of micrometers. For example, a microparticle can have a diameter of less than 1 millimeter (1000 m), or less than about 100 µm.

"Adsorbed" refers to the state of chemical interaction wherein a first species accumulates on the surface of a second species and is bound onto the surface of the second species through surface energy. Typically, it is chemically favorable for the first species to accumulate on the surface of the second species and become adsorbed thereon. Adsorption can occur through either chemisorption or physisorption.

"Number average molecular weight" (Mn) refers to a molecular weight measurement that is calculated by dividing the total weight of all the polymer molecules in a sample with the total number of polymer molecules in the sample.

"Contact angle" refers to an angle formed between a horizontal solid surface and the liquid surface of a droplet maintaining a lens shape when placed on the solid surface. The lens shape and contact angle are characteristic of the liquid and solid surface properties.

"Microfluidic channel" refers to a channel or vessel for carrying or holding fluid, wherein the width of the channel across its narrowest dimension is in the range of millimeters or nanometers. For example, a microfluidic channel can be less than 10 mm, 5 mm, 2 mm, 1 mm, 500 nm, 200 nm, 100 nm, or 50 nm across in its narrowest dimension.

"Emulsion" refers to a mixture of two or more fluids that are normally immiscible. An emulsion can include a first phase in a second phase, such as an aqueous phase in an oil phase. In some cases, an emulsion includes more than two phases. An emulsion can include particulates that function to stabilize the emulsion, and/or function as a coating, such as a droplet skin.

"Droplet" refers to small volume of liquid, typically with a spherical shape, encapsulated by an immiscible fluid, such as a continuous phase or carrier liquid of an emulsion. The volume of a droplet, and/or the average volume of droplets in an emulsion can be, for example, less than one microliter (i.e., a "microdroplet"), less than one nanoliter, or less than one picoliter, among others. A droplet can have a diameter (or the droplets in an emulsion can have an average diameter) of less than 1000, 100, or 10 micrometers, among others. A droplet can be spherical or nonspherical. A droplet can be a simple droplet or a compound droplet, that is, a droplet in which at least one droplet encapsulates at least one other droplet. Droplets generated from an orifice can be monodisperse (composed of droplets of at least generally uniform size) or polydisperse.

The droplets of an emulsion can have any uniform or non-uniform distribution in the continuous phase. If non-uniform, the concentration of the droplets can vary to provide one or more regions of higher droplet density and one or more regions of lower droplet density in the continuous phase. For example, droplets can sink or float in the continuous phase, can be clustered in one or more packets along a channel, can be focused toward the center or perimeter of a flow stream, or the like.

"Nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known nucleotide analogs or modified backbone residues or linkages, which are synthetic, naturally occurring, and non-naturally occurring, that have similar binding properties as the reference nucleic acid and are metabolized in a manner similar to reference nucleotides. Examples of such analogs include, without limitation, phosphorothioates, phosphoramidates, methyl phosphonates, chiral-methyl phosphonates, 2-O-methyl ribonucleotides, and peptide nucleic acids (PNAs). Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., (191) *Nucleic Acid Res.* 19:5081; Ohtsuka et al., (1985) *J. Biol. Chem.* 260:2605; and Rossolini et al., (1994) *Mol. Cell. Probes* 8:91).

Non-limiting examples of polynucleotides or nucleic acids include DNA, RNA, coding or noncoding regions of a gene or gene fragment, intergenic DNA, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), small nucleolar RNA(snoRNA), ribozymes, deoxynucleotides (dNTPs), or dideoxynucleotides (ddNTPs). Polynucleotides can also include complementary DNA (cDNA), which is a DNA representation of mRNA, usually obtained by reverse transcription of messenger RNA (mRNA) or by amplification. Polynucleotides can also include DNA molecules produced synthetically or by amplification, genomic DNA (gDNA), recombinant polynucleotides, branched polynucleotides, plasmids, vectors, isolated DNA of any sequence, isolated RNA of any sequence, nucleic acid probes, or primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component. Polynucleotide sequences, when provided, are listed in the 5' to 3' direction, unless stated otherwise.

Nucleic acids or polynucleotides can be double- or triple-stranded nucleic acids, as well as single-stranded molecules. In double- or triple-stranded nucleic acids, the nucleic acid strands need not be coextensive, for example, a double-stranded nucleic acid need not be double-stranded along the entire length of both strands.

Nucleic acid modifications can include addition of chemical groups that incorporate additional charge, polarizability, hydrogen bonding, electrostatic interaction, and functionality to the individual nucleic acid bases or to the nucleic acid as a whole. Such modifications include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

Nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

"Polymerase chain reaction" or "PCR" refers to a method whereby a specific segment or subsequence of a target double-stranded DNA is amplified in a geometric progression. PCR is well known to those of skill in the art; See, e.g., U.S. Pat. Nos. 4,683,195 and 4,683,202; and PCR Protocols: A Guide to Methods and Applications, Innis et al., eds, 1990. Exemplary PCR reaction conditions typically comprise either two- or three-step cycles. Two-step cycles have a denaturation step followed by a hybridization/elongation step. Three-step cycles comprise a denaturation step followed by a hybridization step followed by a separate elongation step. PCR can be performed as end-point PCR (only monitored at an end point) or as quantitative PCR (monitored in "real time").

"Polymerase" refers to an enzyme that performs template-directed synthesis of polynucleotides. The term encompasses both a full length polypeptide and a domain that has polymerase activity. DNA polymerases are well-known to those skilled in the art, and include but are not limited to DNA polymerases isolated or derived from *Pyrococcus furiosus*, *Thermococcus litoralis*, and *Thermotoga maritime*, or modified versions thereof. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases—DNA polymerases α, δ, and ε—are implicated in nuclear replication, and a family A polymerase—polymerase γ—is used for mitochondrial DNA replication. Other types of DNA polymerases include phage polymerases. Similarly, RNA polymerases typically include eukaryotic RNA polymerases I, II, and III; and bacterial RNA polymerases as well as phage and viral polymerases. RNA polymerases can be DNA-dependent and RNA-dependent.

"Oil" refers to any liquid compound or mixture of liquid compounds that is immiscible with water and that has the majority of its molecular weight in the form of carbon. In some examples, oil also has its non-carbon molecular weight in the form of hydrogen, fluorine, silicon, oxygen, or any combination thereof, among others.

DETAILED DESCRIPTION

I. General

The present invention provides modified polymer surfaces that have a high water contact angle and a high resistance to degradation or fouling upon exposure to protein solutions. The inventors have discovered particular coating compositions that are capable of providing a robust surface modification that improves interfacial surface tension and biofouling resistance. The present invention also provides microfluidic devices having an interior surface that includes a provided coated polymer surface, methods of moving an emulsion of droplets through a microfluidic channel of a provided microfluidic device, methods for producing the provided coated polymer surfaces, and compositions of the coating itself.

II. Coatings

Several coatings for modifying the surface properties of polymer surfaces, such as those used in the fabrication of microfluidic devices, are provided herein. The coatings include a silicone polymer and hydrophobic silica. Prior to application to a surface, the coatings can further include a solvent in which the silicone polymer and hydrophobic silica are dissolved or dispersed. In some embodiments, the solvent is a silicone oil.

The silicone polymer can be selected to have properties beneficial for use in microfluidic devices. These properties can include high solvent resistance and low moisture adsorption. The silicone polymer can be a homopolymer or copolymer having the formula:

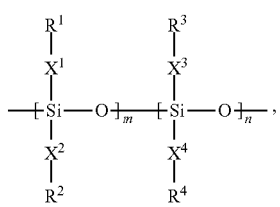

wherein $R^1$, $R^2$, $R^3$, and $R^4$ can each independently be hydrogen, halogen, $C_{1-18}$ alkyl, $C_{2-18}$ alkenyl, $C_{1-18}$ haloalkyl, $C_{3-10}$ cycloalkyl, $C_{3-8}$ heteroycloalkyl, $C_{6-12}$ aryl, or $-NH_2$. $X^1$, $X^2$, $X^3$, and $X^4$ can each independently be absent or $C_{1-6}$ alkylene. Subscripts m and n can each independently be integers that are 0 or are greater than 20, wherein at least one of m and n is greater than 20. The silicone polymer can be a graft copolymer. The silicone polymer can be linear or branched. Nonlimiting examples of silicone polymers include polydimethylsiloxane, polymethyl-(3,3,3-trifluoropropyl)siloxane, polymethylphenylsiloxane, poly(3-aminopropyl)methylsiloxane, polydiphenyl siloxane, poly(2-(3,4-epoxycyclohexyl)ethyl)methylsiloxane, polymethylhydrosiloxane, polymethyl(3-hydroxypropyl)siloxane, poly(3-(2-(2-hydroxyethoxy)ethoxy)propyl)methylsiloxane, and copolymers thereof. In some embodiments, the silicone polymer of the coating composition is polydimethylsiloxane (PDMS).

The molecular weight of the silicone polymer can be within the range from 1000 to 10,000 Da, e.g., from 1000 to 6000 Da, from 2000 to 7000 Da, from 3000 to 8000 Da, from 4000 to 9000 Da, or from 5000 to 10,000 Da. The molecular weight of the silicone polymer can be within the range from 3000 to 4000 Da, e.g., from 3000 to 3600 Da, from 3100 to 3700 Da, from 3200 to 3800 Da, from 3300 to 3900 Da, or from 3400 to 4000 Da. The silicone polymer can have, for example, vinyl-terminated ends or methyl-terminated ends. In some embodiments, the silicone polymer has trimethylated ends.

The hydrophobic silica of the coating composition can have any hydrophobic groups chemically bonded to its silicon dioxide surface. The hydrophobic groups can be organosiloxane chains, such as for example, polydimethylsiloxane chains. The hydrophobic groups can be alkyl chains, such as for example, $C_{8-20}$-alkyl. The hydrophobic groups can be $C_{12}$-alkyl, $C_{14}$-alkyl, $C_{16}$-alkyl, $C_{18}$-alkyl, or $C_{20}$-alkyl. The hydrophobic silica can be, for example, fumed silica or precipitated silica. The hydrophobic silica particles can be, for example, nanoparticles having an average diameter within the range from 5 to 60 nm, from 15 to 70 nm, from 25 to 80 nm, from 35 to 90 nm, or from 45 to 100 nm. In some embodiments, the hydrophobic silica particles have an average diameter within the range from 5 to 100 nm. The hydrophobic silica particles can be, for example, microparticles having an average diameter within the range from 1 to 3 µm, from 1.5 to 3.5 µm, from 2 to 4 µm, from 2.5 to 4.5 µm, or from 3 to 5 µm. In some embodiments, the hydrophobic silica particles have an average diameter within the range from 1 to 5 µm.

The mass ratio of the silicone polymer to the hydrophobic silica in the coating can be selected as desired. In some embodiments, the mass ratio is within the range from 1:1 to 1:100, e.g., from 1:1 to 2:1, from 1.5:1 to 2.5:1, from 2:1 to 4:1, from 2.5:1 to 15:1, or from 4:1 to 100:1. The mass ratio of the silicone polymer to the hydrophobic silica can be within the range from 1.7:1 to 4.5:1, e.g., from 1.7:1 to 2.5:1, from 1.8:1 to 3:1, from 1.9:1 to 3.5:1, from 2:1 to 4:1, or from 2.1:1 to 4.5:1. The combined mass concentration of the silicone polymer and hydrophobic silica in the silicone oil or other solvent can be within the range from 0.1% to 10% weight/weight, e.g., from 0.1% to 1.6%, from 0.2% to 2.5%, from 0.3% to 4%, from 0.4% to 6.3%, or from 0.6% to 10% weight/weight. The combined mass concentration of the silicone polymer and hydrophobic silica in the silicone oil or other solvent can be within the range from 0.4% to 2.5% weight/weight, e.g., from 0.4% to 1.2%, from 0.5% to 1.4%, from 0.6% to 1.7%, from 0.7% to 2.1%, or from 0.8% to 2.5% weight/weight.

The silicone oil can be a low molecular weight silicone oil selected for its ability to dissolve or disperse the silicone polymer and hydrophobic silica of the coating mixture. Nonlimiting examples of silicone oils include polydimethylsiloxanes and polymethylphenylsiloxanes. The molecular weight of the silicone oil of the coating can be within the range from 100 to 1600, e.g., from 100 to 1000, from 250 to 1150, from 400 to 1300, from 550 to 1450, or from 700 to 1600. The molecular weight of the silicone oil of the coating can be within the range from 100 to 600, e.g., from 100 to 400, from 150 to 450, from 200 to 500, from 250 to 550, or from 300 to 600. In some embodiments, the silicone oil is hexamethyldisiloxane.

III. Coated Polymer Surfaces

Also provided are several coated polymer surfaces that include a substrate layer and a coating layer. The substrate layer includes a hydrophobic polymer, and the coating layer includes a silicone polymer and hydrophobic silica as described above. The coating layer is adsorbed to at least a portion of the substrate layer through noncovalent attachments. The composition of the silicone polymer and hydrophobic silica, the number average molecular weight of the silicone polymer, the average diameter of the hydrophobic silica, and the mass ratio of the silicone polymer to hydrophobic silica in the coating layer can be as described above. In some embodiments, the coating layer includes polydimethylsiloxane and hydrophobic silica, wherein the molecular weight of the silicone polymer is within the range from 1000 Da to 10,000 Da, and wherein the mass ratio of polydimethylsiloxane to hydrophobic silica in the coating layer is within the range from 1.5:1 to 15:1. In some embodiments, the coating layer includes polydimethylsiloxane and hydrophobic silica, wherein the molecular weight of the silicone polymer is within the range from 3000 Da to 4000 Da, and wherein the mass ratio of polydimethylsiloxane to hydrophobic silica in the coating layer is within the range from 1.7:1 to 4.5:1.

The hydrophobic surface polymer can be selected, for example, to have properties beneficial for application in microfluidic devices. These can include high solvent resistance, low moisture adsorption, low dielectric loss, and adequate optical clarity. The surface polymer can be, for example, polymethylmethacrylate (PMMA), polydimethylsiloxane (PDMS), polyethylene terephthalate (PET), polycarbonate (PC), polybutylene terephthalate, polyethylene, polypropylene (PP), cyclic olefin polymer (COP), or cyclic olefin copolymer (COP). In some embodiments, the hydrophobic polymer is COP. In some embodiments, the hydrophobic polymer is COC. The hydrophobic surface polymer can be a copolymer. The surface polymer can be grafted with one or more chemistries of side chains, e.g., fluorinated or acrylic side chains, that can enhance the performance of the surface polymer in microfluidic applications. In some embodiments, the surface to which the coating is applied is not a polymer surface, but is instead another material type, such as for example, glass.

The coating layer can be a monolayer of silicone polymer with hydrophobic silica dispersed within. The coating layer can have multiple layers of silicone polymer and hydrophobic silica. The coating layer can have a thickness that is less than 50 µm, less than 40 µm, less than 30 µm, less than 20 µm, less than 10 µm, less than 5 µm, less than 2 µm, less than 1 µm, less than 500 nm, less than 250 nm, less than 100 nm, less than 50 nm, less than 30 nm, less than 20 nm, or less than 10 nm. In some embodiments, the coating layer thickness is within the range from 10 nm to 50 µm, e.g., from 10 nm to 2 µm, from 20 nm to 4 µm, from 50 nm to 9 µm, from 100 nm to 20 µm, or from 300 nm to 50 µm. In some embodiments, the coating layer thickness is within the range from 100 nm to 4 µm, e.g., from 100 nm to 1 µm, from 200 nm to 1.5 µm, from 300 nm to 2 µm, from 400 nm to 3 µm, or from 500 nm to 4 µm.

The water contact angle of the coated polymer surface is a measure of the hydrophobicity of the surface. As discussed above, surfaces with more hydrophobic properties are more suitable for use with applications in which the integrity of an aqueous phase, such as that of a droplet, within a nonaqueous phase is to be maintained. The water contact angle of the coated polymer surface can be greater than 94°, greater than 96°, greater than 98°, greater than 100°, greater than 102°, greater than 104°, greater than 106°, greater than 108°, greater than 110°, greater than 112°, greater than 114°, greater than 116°, greater than 118°, or greater than 120°. In some embodiments, the water contact angle of the coated polymer surface is greater than 100°.

The biofouling of a polymer surface can negatively influence its desired hydrophobic properties. The specific configuration of the coating described herein can mitigate these biofouling effects when used to modify a polymer surface. A suitable test of the ability of a polymer surface to resist biofouling is to measure and compare the water contact angles of the surface both before and after exposure to a proteinaceous aqueous solution. For example, the surface can be exposed to an aqueous 1 mg/mL bovine serum albumin (BSA) solution or gelatin solution for a period of 1 hour, with the water contact angles prior to and subsequent to this exposure determined. As a result of the coating, upon exposure to this BSA or gelatin solution, the modified polymer surface can exhibit a change in its water contact angle of less than 20°, less than 18°, less than 16°, less than 14°, less than 12°, less than 10°, less than 8°, less than 6°, less than 4°, or less than 2°. In some embodiments, the coated polymer surface has a water contact angle that changes by less than 10° upon exposure to an aqueous 1 mg/mL bovine serum albumin solution for 1 hour.

IV. Methods of Producing Coated Polymer Substrates

Also provided are several methods of producing the coated polymer surfaces described herein. The methods include contacting a substrate layer with a mixture that includes a silicone polymer, a silicone oil, and hydrophobic silica, such that at least a portion of the silicone polymer and hydrophobic silica adsorb to the substrate layer. The substrate layer includes a hydrophobic polymer. Optionally, the method further includes flushing from the substrate layer the silicone polymer, silicone oil, and hydrophobic silica not adsorbed to the substrate layer, thereby producing the coated polymer surface. The composition of the silicone polymer, silicone oil, and hydrophobic silica, the number average molecular weight of the silicone polymer, the average diameter of the hydrophobic silica, the mass ratio of the silicone polymer to hydrophobic silica in the coating layer, and the water contact angle and biofouling resistance of the coated polymer surface are as described above. In some embodiments, the coating mixture of the method includes polydimethylsiloxane and hydrophobic silica, wherein the molecular weight of the silicone polymer is within the range from 1000 Da to 10,000 Da, and wherein the mass ratio of polydimethylsiloxane to hydrophobic silica in the coating layer is within the range from 1.5:1 to 15:1. In some embodiments, the coating mixture of the method includes polydimethylsiloxane and hydrophobic silica, wherein the molecular weight of the silicone polymer is within the range from 3000 Da to 4000 Da, and wherein the mass ratio of polydimethylsiloxane to hydrophobic silica in the coating layer is within the range from 1.7:1 to 4.5:1.

The contacting of the substrate layer with the coating mixture can be for a period of less than 1 minute, less than 2 minutes, less than 3 minutes, less than 4 minutes, less than 5 minutes, less than 10 minutes, less than 15 minutes, less than 20 minutes, less than 25 minutes, less than 30 minutes, less than 1 hour, less than 2 hours, less than 3 hours, less than 4 hours, less than 5 hours, less than 10 hours, or less than 1 day. The contacting time can be within the range from 1 minute to 1 hour, e.g., from 1 to 20, from 10 to 30, from 20 to 40, from 30 to 50, or from 40 to 60 minutes. For applications in which the polymer surface is the interior surface of a microfluidic channel, the contacting can include flowing the coating dispersion through the microfluidic channel. The flow can be at any flow rate configured to result in the contacting time periods described above. The flow of the coating mixture through the microfluidic channel can be a recirculating flow.

The coated polymer surface can be flushed subsequent to the contacting of the substrate layer and the coating mixture to remove those components of the coating mixture that did not adsorb to the substrate layer during the contacting. The flushing can include flowing a material over the coated polymer surface. For applications in which the polymer surface is the interior surface of a microfluidic channel, the flushing can include flowing a material through the microfluidic channel. The fluid passed over the coated polymer surface or through the microfluidic channel can be a liquid or a gas. In some embodiments, the flushing includes passing air over the substrate layer.

In some embodiments, the method further includes washing the coated polymer surface subsequent to the flushing of material from the substrate layer. The additional washing step can further ensure that substantially only those components of the coating mixture having a particular affinity for the substrate layer remain with the coated polymer surface. The washing can be for a period of less than 1 minute, less than 2 minutes, less than 3 minutes, less than 4 minutes, less than 5 minutes, less than 10 minutes, less than 15 minutes, less than 20 minutes, less than 25 minutes, less than 30 minutes, less than 1 hour, less than 2 hours, less than 3 hours, less than 4 hours, less than 5 hours, less than 10 hours, or less than 1 day. The washing time can be within the range from 1 minute to 1 hour, e.g., from 1 to 20, from 10 to 30, from 20 to 40, from 30 to 50, or from 40 to 60 minutes. For applications in which the polymer surface is the interior surface of a microfluidic channel, the contacting can include flowing the coating dispersion through the microfluidic channel. The flow can be at any flow rate configured to result in the contacting time periods described above. The flow of the coating mixture through the microfluidic channel can be a recirculating flow.

In some embodiments, a cleaning solvent is used to wash the coated polymer surface. The cleaning solvent can be selected for its ability to solubilize fluorocarbons or hydrocarbons, and its compatibility with acrylics and silicones. The cleaning solvent can be, for example, a fluorinated solvent. In some embodiments, the fluorinated solvent is 1,1,1,2,2,3,3,4,4-nonafluoro-4-methoxybutane (NOVEC 7100, registered trademark, manufactured by 3M Limited).

V. Microfluidic Devices

As discussed above, the coated polymer surfaces described herein are particularly useful elements for the fabrication of microfluidic devices that handle emulsions with distinct aqueous and nonaqueous phases. Accordingly, also provided are microfluidic channels having an interior polymer surface. The interior polymer surface includes a hydrophobic polymer substrate, and a coating that includes a silicone polymer and hydrophobic silica. The composition of the hydrophobic polymer, silicone polymer, and hydrophobic silica, the number average molecular weight of the silicone polymer, the average diameter of the hydrophobic silica, the mass ratio of the silicone polymer to hydrophobic silica in the coating layer, and the water contact angle and biofouling resistance of the coated polymer surface are as described above.

Further provided are microfluidic devices that include such a microfluidic channel. The microfluidic devices can use the microfluidic channel for transporting or otherwise manipulating emulsions of droplets. For example, the microfluidic devices can be used for methods of interleaving droplets, methods of increasing and decreasing the volume of immiscible fluid in an emulsion (thereby decreasing or increasing the density of droplets, respectively), methods of filtering emulsions, and methods of tracking and/or separating sets of droplets. Other functions of the microfluidic devices can include mixing, splitting, sorting, heating, and so forth. The microfluidic channels of the device are typically of uniform cross section in the mm, µm, or nm scale. The inlet and outlet of each microfluidic channel can be of any shape, including but not limited to, circular, elliptical, triangular, rectangular and so forth. The microfluidic channels can have an average cross-sectional dimension, for example, of less than about 1 mm, less than about 100 µm, less than about 10 µm, less than about 1 µm, less than about 100 nm, less than about 10 nm, and so forth. Other aspects of microfluidic devices are disclosed in, for example, U.S. Patent Application Publication No. 2015/0065396, which is incorporated by reference in its entirety for all purposes.

In some embodiments, substantially all of the microfluidic channels or microfluidic channel regions of a microfluidic device include a coated polymer surface as described herein. In some embodiments, a portion of the microfluidic channels or microfluidic channel regions of a microfluidic device include a coated polymer surface as described herein.

VI. Methods of Moving Droplet Emulsions

Also provided are methods for moving an emulsion of droplets through a microfluidic channel. The method includes providing a microfluidic device, wherein the microfluidic device includes a microfluidic channel. The microfluidic channel includes an interior surface, wherein the interior surface includes a coated polymer surface. The coated polymer surface includes a substrate layer with a hydrophobic polymer, and a coating layer with a silicone polymer an hydrophobic silica. The method further includes providing an emulsion, wherein the emulsion includes droplets and an emulsion fluid. The method further includes providing a force sufficient to move the emulsion through the microfluidic channel of the microfluidic device.

The emulsions can be, for example, water-oil emulsions. Exemplary emulsions include those used, for example, in applications such as DNA sequencing, in which an individual polymerase chain reaction (PCR) can be carried out in each or several distinct aqueous droplets of a water-oil emulsion. Exemplary DNA sequencing applications include digital PCR or droplet digital PCR (DDPCR). The emulsions can include two phases, or more than two phases. The method can also be applied to applications including multiple emulsions, each of which can have two or more phases. The compositions of different phases in different emulsions can be identical, similar, or different. The emulsions can have additional components, including one or more surfactant, reagent, sample, label, particle, or combinations thereof. In some embodiments, the oil is or includes at least one silicone oil, mineral oil, fluorocarbon or fluorinated oil, vegetable oil, or a combination thereof, among others.

Emulsions can be characterized by a predominant liquid compound or type of liquid compound in each phase. In some embodiments, the predominant liquid compounds in the emulsion are water and oil. In some embodiments, the emulsion comprises droplets of the aqueous phase disposed in a nonaqueous continuous phase. In some embodiments, an emulsion is formed comprising droplets of the nonaqueous phase disposed in an aqueous continuous phase. In some embodiments, an interfacial skin is created between each droplet and the continuous phase, to transform the droplets into capsules. In some embodiments, the provided aqueous phase includes skin-forming proteins and at least one surfactant. In some embodiments, the emulsion further includes a spacing fluid that is miscible with the continuous phase and has a different composition than that of the continuous phase. Exemplary descriptions of DDPCR emulsion components can be found in U.S. Patent Application No. 2014/0302503, which is entirely incorporated herein by reference for all purposes. Exemplary descriptions of emulsion formation methods can be found in U.S. Patent Application No. 2012/0152369, which is entirely incorporated herein by reference for all purposes. Any of the emulsions disclosed herein can be monodisperse—composed of droplets of at least generally uniform size—or can be polydisperse—composed of droplets of various sizes. Droplets generated from an orifice similarly can be monodisperse or polydisperse.

In some embodiments, the W/O emulsion droplets are substantially uniform in shape and/or size. For example, in some embodiments, the droplets are substantially uniform in average diameter. For example, in some embodiments, at least 50%, 60%, 70%, 75%, 80%, 85%, 90%, or 95% of the droplets in the population are within 5% of the average droplet size (diameter) of the population. In some embodiments, the droplets have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the number of droplets in the W/O emulsion is at least about 100; 1,000; 5,000; 10,000; 25,000; 50,000; 100,000; $1\times10^6$; or $1\times10^7$. In some embodiments, the number of droplets is from about 100 to about $1\times10^7$, from about 1,000 to about $1\times10^7$, from about 1,000 to about $1\times10^6$, from about 10,000 to about $1\times10^7$, from about 10,000 to about $1\times10^6$, from about 10,000 to about $1\times10^5$, from about 20,000 to about $1\times10^6$, or from about 20,000 to about $1\times10^5$.

At least a portion of the droplets of the emulsion can include nucleic acids. At least a portion of the droplets can include reagents sufficient for a PCR. The reagents for PCR can include a polymerase enzyme. Any suitable PCR technology or combination of technologies can be utilized with the devices and methods disclosed herein. These PCR technologies include allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation-specific PCR, miniprimer PCR, multiplex ligation-dependent probe amplification, multiplex PCR, nested PCR, overlap extension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, among others.

At least a portion of the droplets of the emulsion can include an enzyme or other reagents sufficient for reactions other than PCR. Any suitable enzyme-catalyzed reactions can be performed with the devices and methods disclosed herein. For example, the reactions can be catalyzed by a kinase, nuclease, nucleotide cyclase, nucleotide ligase, nucleotide phosphodiesterase, polymerase (DNA or RNA), phenyl transferase, pyrophospatase, reporter enzyme (e.g., alkaline phosphatase, beta-galactosidase, chloramphenicol acetyl transferase, glucuronidase, horse radish peroxidase, luciferase, etc.), reverse transcriptase, topoisomerase, or other.

The droplets can contain reagents for detection of biological analytes, including but not limited to a protein such as a fluorescent protein and/or an antibody. In some cases, a plurality of droplets described herein contain a plurality of different fluorescent dyes, or fluorescent dye concentrations, or a combination thereof. The use of different fluorescent dyes and/or concentrations of fluorescent dyes can provide for highly multiplex analysis.

VII. Examples

Example 1. Surface Modification with a Coating of PDMS and Hydrophobic Silica

A coating mixture of 3000-4000 Da PDMS and hydrophobic silica in hexamethyldisiloxane was prepared by dissolving or dispersing the two reagents in the silicone oil at a combined concentration of 1% weight/weight. The hydrophobic silica was present in the coating mixture at roughly 40% weight/weight of the neat polymer (giving a mass ratio of PDMS to hydrophobic silica of 2.5:1). The coating mixture was then contacted with the COP microfluidic surfaces of a device by flowing the mixture through the microfluidic channels of the device. After all of the microfluidic channels had been filled with the coating mixture, the device was flushed with air, removing excess coating mixture. Subsequent washes with NOVEC 7100 were used to further remove residual silicone oil from the microfluidic surfaces.

The water contact angle of the surfaces were measured in triplicate, both before and after the surface treatment, using 2.5 µL water for each measurement. Results showed that the untreated COP surfaces had a water contact angle of approximately 90°, while the same surfaces after treatment with the coating of PDMS and hydrophobic silica had a water contact angle of approximately 115°.

Coated and uncoated polymer surfaces were then contacted with an aqueous 1 mg/mL bovine serum albumin (BSA) solution for 1 hour. After this exposure, the surfaces were washed with water and then blown dry. The water contact angle of each surface was then measured again in triplicate using 2.5 µL water for each measurement. Results showed that the COP surfaces treated with the coating of PDMS and hydrophobic silica and exposed to the proteinaceous solution had a water contact angle that remained at approximately 115°. In contrast, the untreated COP surfaces that were exposed to the proteinaceous solution had a water contact angle that decreased from the initial value of approximately 90° to a value of approximately 20°. These data show the ability of the particular coating solution of PDMS and hydrophobic silica to increase the resistance of coated surfaces to biofouling of the type that can be common in microfluidic applications.

Example 2. Surface Modification with a Coating of PDMS

A coating mixture of 3000-4000 Da PDMS in hexamethyldisiloxane was prepared by dissolving the silicone polymer in the silicone oil at a concentration of 1% weight/weight. The coating mixture was then contacted with the COP microfluidic surfaces of a device by flowing the mixture through the microfluidic channels of the device. After all of the microfluidic channels had been filled with the coating mixture, the device was flushed with air, removing excess coating mixture. Subsequent washes with NOVEC 7100 were used to further remove residual silicone oil from the microfluidic surfaces.

The water contact angle of the surfaces were measured in triplicate, both before and after the surface treatment, using 2.5 µL water for each measurement. Results showed that the untreated COP surfaces had a water contact angle of approximately 90°, while the same surfaces after treatment with the coating of PDMS had a water contact angle of approximately 110°. This treated surface then has a water contact angle that is slightly lower than that of the surface treated with both PDMS and hydrophobic silica as in Example 1.

Coated and uncoated polymer surfaces were then contacted with an aqueous 1 mg/mL bovine serum albumin (BSA) solution for 1 hour. After this exposure, the surfaces were washed with water and then blown dry. The water contact angle of each surface was then measured again in triplicate using 2.5 µL water for each measurement. Results showed that the COP surfaces treated with the coating of PDMS and exposed to the proteinaceous solution had a water contact angle that decreased to 500. This drop in hydrophobicity in response to the BSA solution is lower than that observed with the untreated COP surface (Example 1). The decrease is in sharp contrast, though, to the BSA response of the COP surface treated with both PDMS and hydrophobic silica, for which no appreciable decrease in water contact angle was observed. These data show that while a coating of PDMS alone does have the ability to somewhat increase the hydrophobicity of a polymer surface, it has a more limited ability to increase the resistance of coated surfaces to biofouling of the type that can be common in microfluidic applications.

Example 3. Surface Modification with a Coating of Hydrophobic Silica

A coating mixture of hydrophobic silica in hexamethyldisiloxane was prepared by dissolving the silica in the silicone oil at a concentration of 1% weight/weight. The coating mixture was then contacted with the COP microfluidic surfaces of a device by flowing the mixture through the microfluidic channels of the device. After all of the microfluidic channels had been filled with the coating mixture, the device was flushed with air, removing excess coating mixture. Subsequent washes with NOVEC 7100 were used to further remove residual silicone oil from the microfluidic surfaces.

The water contact angle of the surfaces were measured in triplicate, both before and after the surface treatment, using 2.5 µL water for each measurement. Results showed that the untreated COP surfaces had a water contact angle of approximately 90°, while the same surfaces after treatment with the coating of hydrophobic silica had a water contact angle of approximately 160°. This treated surface then has a water contact angle that is much higher than that of the surface treated with both PDMS and hydrophobic silica as in Example 1, and the surface treated with PDMS alone as in Example 2.

Coated and uncoated polymer surfaces were then contacted with an aqueous 1 mg/mL bovine serum albumin (BSA) solution for 1 hour. After this exposure, the surfaces were washed with water and then blown dry. The water contact angle of each surface was then measured again in triplicate using 2.5 µL water for each measurement. Results showed that the COP surfaces treated with the coating of hydrophobic silia and exposed to the proteinaceous solution had a water contact angle that decreased to 20°. This drop in hydrophobicity in response to the BSA solution is much higher than that observed with the COP surfaces treated with both PDMS and hydrophobic silica (Example 1) and the surfaces treated with PDMS alone (Example 2). These data show that while a coating of hydrophobic silica alone does have the ability to significantly increase the hydrophobicity of a polymer surface, it does not have the ability to increase the resistance of coated surfaces to biofouling of the type that can be common in microfluidic applications.

The results from Example 1, Example 2, and Example 3 are summarized in Table 1 below. From the Table it can be clearly seen that of the three tested coatings, only the coating that has the particular combination of PDMS and hydrophobic silica is able to produce a coated polymer surface that has both an improved hydrophobicity and an improved biofouling resistance.

TABLE 1

| Coating Components | Initial Water Contact Angle | Water Contact Angle After BSA Exposure |
| --- | --- | --- |
| No coating | 90° | 20° |
| PDMS + Hydrophobic Silica | 115° | 115° |
| PDMS | 110° | 50° |
| Hydrophobic Silica | 160° | 20° |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A coated polymer surface comprising:
   a substrate layer comprising cyclic olefin polymer (COP) or cyclic olefin copolymer (COC); and
   a coating layer comprising a silicone polymer and hydrophobic silica, wherein the coating layer is adsorbed to at least a portion of the substrate layer.

2. The coated polymer surface of claim 1, wherein the number average molecular weight of the silicone polymer is within the range from 1000 Da to 10,000 Da.

3. The coated polymer surface of claim 1, wherein the mass ratio of silicone polymer to hydrophobic silica in the coating layer is within the range from 1.5:1 to 15:1.

4. The coated polymer surface of claim 1, wherein the silicone polymer is polydimethylsiloxane.

5. The coated polymer surface of claim 1, wherein the coated polymer surface has a water contact angle of greater than 100°.

6. The coated polymer surface of claim 5, wherein the water contact angle changes by less than 10° upon exposure to an aqueous 1 mg/mL bovine serum albumin solution for 1 hour.

7. The coated polymer surface of claim 1, wherein the substrate layer comprises COP, wherein the coating layer comprises polydimethylsiloxane and hydrophobic silica, wherein the molecular weight of the silicone polymer is within the range from 1000 Da to 10,000 Da, and wherein the mass ratio of polydimethylsiloxane to hydrophobic silica in the coating layer is within the range from 1.5:1 to 15:1.

8. A method of moving an emulsion of droplets through a microfluidic channel, the method comprising:
provinding a device comprising a microfluidic channel having an interior surface, wherein the interior surface comprises the coated polymer surface of claim 1;
providing an emulsion comprising droplets and a emulsion fluid;
providing a force sufficient to move the emulsion through the microfluidic channel of the device.

9. The method of claim 8, wherein the droplets are aqueous droplets comprising nucleic acids and reagents sufficient for a polymerase chain reaction.

10. The method of claim 8, wherein the emulsion fluid comprises a fluorinated oil or a silicone oil.

* * * * *